United States Patent
D'Acchioli et al.

(10) Patent No.: US 6,951,552 B2
(45) Date of Patent: Oct. 4, 2005

(54) DIAPERING SYSTEM: DIAPER AND INTEGRAL COLLECTOR

(75) Inventors: Vincenzo D'Acchioli, Kelkheim/Ts. (DE); Gianfranco Palumbo, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 239 days.

(21) Appl. No.: 10/239,531

(22) PCT Filed: Mar. 19, 2001

(86) PCT No.: PCT/US01/08758

§ 371 (c)(1),
(2), (4) Date: Sep. 23, 2002

(87) PCT Pub. No.: WO01/70156

PCT Pub. Date: Sep. 27, 2001

(65) Prior Publication Data

US 2003/0208170 A1 Nov. 6, 2003

(30) Foreign Application Priority Data

Mar. 21, 2000 (EP) .............................. 00105381

(51) Int. Cl.⁷ ................................ A61F 13/15
(52) U.S. Cl. ...................................... 604/319
(58) Field of Search ................ 604/332–356, 604/385.01, 385.19; 4/144.1, 144.2, 144.3, 144.4

(56) References Cited

U.S. PATENT DOCUMENTS

| | | |
|---|---|---|
| 3,292,626 A | 12/1966 | Schneider |
| 3,522,807 A | 8/1970 | Millenbach |
| 3,532,093 A | 10/1970 | Lovret |
| 3,577,989 A | 5/1971 | Anderson |
| 3,734,096 A | 5/1973 | Millenbach |
| 3,860,003 A | 1/1975 | Buell |
| 4,781,713 A | 11/1988 | Welch et al. |
| 4,784,656 A | 11/1988 | Christian |
| 4,804,377 A | 2/1989 | Hanifl et al. |
| 5,520,674 A | 5/1996 | Lavon et al. |
| 6,132,409 A * | 10/2000 | Vogt et al. ................... 604/348 |
| 6,468,256 B1 * | 10/2002 | Mishima ................ 604/385.14 |

FOREIGN PATENT DOCUMENTS

| | | |
|---|---|---|
| EP | 0 245 064 A2 | 11/1987 |
| EP | 0 887 061 A1 | 12/1998 |
| EP | 0 966 933 A1 | 12/1999 |
| FR | 2 495 899 A | 6/1982 |
| GB | 2 152 387 A | 8/1985 |
| GB | 2 215 605 A | 9/1989 |
| JP | 08-117261 | 5/1996 |
| SE | 8104934-8 | 5/1986 |
| WO | WO 93/16669 A1 | 9/1993 |
| WO | WO 93/25172 A1 | 12/1993 |

* cited by examiner

Primary Examiner—Larry I. Schwartz
Assistant Examiner—Michael G Bogart
(74) Attorney, Agent, or Firm—Edward J. Milbradia; Ken K. Patel; Steven W. Miller

(57) ABSTRACT

The present invention relates to a diapering system (200) suitable for the collection of urine and faeces. Claimed and described is a diapering system comprising one human waste collection bag integral with one absorbent component (preferably a diaper like absorbent component) located outside of or adjacent to the collection bag.

4 Claims, 4 Drawing Sheets

DIAPERING SYSTEM: DIAPER AND INTEGRAL COLLECTOR

FIELD OF THE INVENTION

The present invention relates to a diapering system. The system comprises only integral components and is suitable for the collection of urine and faeces, thereby providing improved fit and wearing comfort.

BACKGROUND OF THE INVENTION

Human waste collection bags, principally comprising faecal collection bags and urine collection bags, are known articles of manufacture that are designed to be worn principally by incontinence sufferers and in particular by bedridden patients. Such human waste collection bags are attached to the perianal or uro-genital region of the wearer and are intended to entrap and immediately contain faecal material and other bodily discharges.

Representative prior art in the field of faecal collection bags includes the following documents: U.S. Pat. Nos. 3,734,096 and 3,522,807 disclose faecal collection bags provided with adhesive tabs to support the attachment of the collection bag to the human body. GB 2 152 387, GB 2 215 605, SE 8 104 934 and EP 245 064 all disclose collection bags which are made from plastic materials and rely on an principally flat adhesive flange for attachment to and seal with the human body. JP 8-117261 discloses a faecal collection bag, which is attached to the body by sheets of material cut to surround the lower parts of the body similar to a piece of underwear. U.S. Pat. No. 4,784,656 discloses a two piece faecal collection bag. The piece providing the collection capacity can be emptied or replaced while the other piece remains engaged in body contact.

Representative disclosures of urine collection bags are, for instance, found in the following documents: U.S. Pat. No. 4,804,377 discloses a collection bag for urine specimens from children. U.S. Pat. No. 3,292,626 discloses a urine collection bag for female infants.

Some prior art documents disclose devices for multiple incontinence: For example, U.S. Pat. No. 3,577,989 discloses a device for female users comprising a plastic bag for the collection of both, urine and faeces. The bag is provided with a flange portion to cover the urinary duct and the anus, the flange comprising elastic straps for attachment to the body. U.S. Pat. No. 3,532,093 discloses a collector for urine and faeces comprising two attached bags for the respective collection of urine and faeces. Those devices, however, do not comprise any absorbent means within or outside these collection bags. Hence in use these devices easily become a source of leakage and/or of malodour.

The prior art further describes a multitude of diapers, for babies as well as for adults, as disclosed for example in U.S. Pat. No. 3,860,003 and in WO 93/16669. Despite the enormous progress made in providing high capacity absorbent cores, one may however want to provide for some user groups a urine and/or faecal collection bag. As compared to conventional diapers human waste collection bags apart from potentially providing larger capacity in particular provide the benefit of better separation of human waste from the skin of the wearer. Such separation from the skin may also allow for longer wearing times of the device giving a comfort and environmental benefit.

A considerable group of users of incontinence devices is both, urine and faecal incontinent. Those user's namely include babies, but also unhealthy and elderly people. The degree of incontinence is highly individual and may be different with regard to the different kinds of incontinence, i.e. urine or faecal. For example, a wearer may experience slight urine incontinence and severe faecal incontinence or vice versa. Hence, there is a need for a device which can be provided to suit such individual incontinence needs.

As generally known in the art with regard to adhesively attached human waste collection bags, detachment and following reattachment of another human waste collection bag is typically stressful for the skin of the wearer to which the human waste collection bag is attached. It is very desirable to avoid any additional stress or even pain for the skin of the wearer which may be particularly sensitive due to contact with faecal matter or urine. Therefore, it is desirable to provide other and/or additional attachment means for a human waste collection bag, so that less or no adhesive can be employed.

Another problem well known in the art is that of the proper placement of a human waste collection bag, again in particular for those devices designed for adhesive attachment to the wearer's skin. Total or substantial misplacement of the device will lead to a severe misfunctioning, may it be leaking or may it even be unintentional detachment.

In view of the prior art there remains a need for an incontinence device which:

provides improved urine and faecal incontinence care can be provided to suit individual incontinence needs is environmentally friendly provides high objective and subjective reassurance regarding leaking and unintentional detachment is comfortable to wear, for bedridden, but also for active wearer's engages in a reliable seal with the human body, while avoiding stress for the wearer's skin can easily be positioned and applied These and other objectives are addressed by the present invention as apparent from the following description.

SUMMARY OF THE INVENTION

The present invention relates to a diapering system (200) suitable for the collection of urine and faeces. Claimed and described is a diapering system comprising one human waste collection bag integral with one absorbent component (preferably a diaper like absorbent component) located outside of or adjacent to the collection bag.

BRIEF DESCRIPTION OF THE DRAWINGS

It is believed that the invention will be better understood from the foregoing description in conjunction with the accompanying drawings in which.

DETAILED DESCRIPTION OF THE INVENTION

Figure 1:
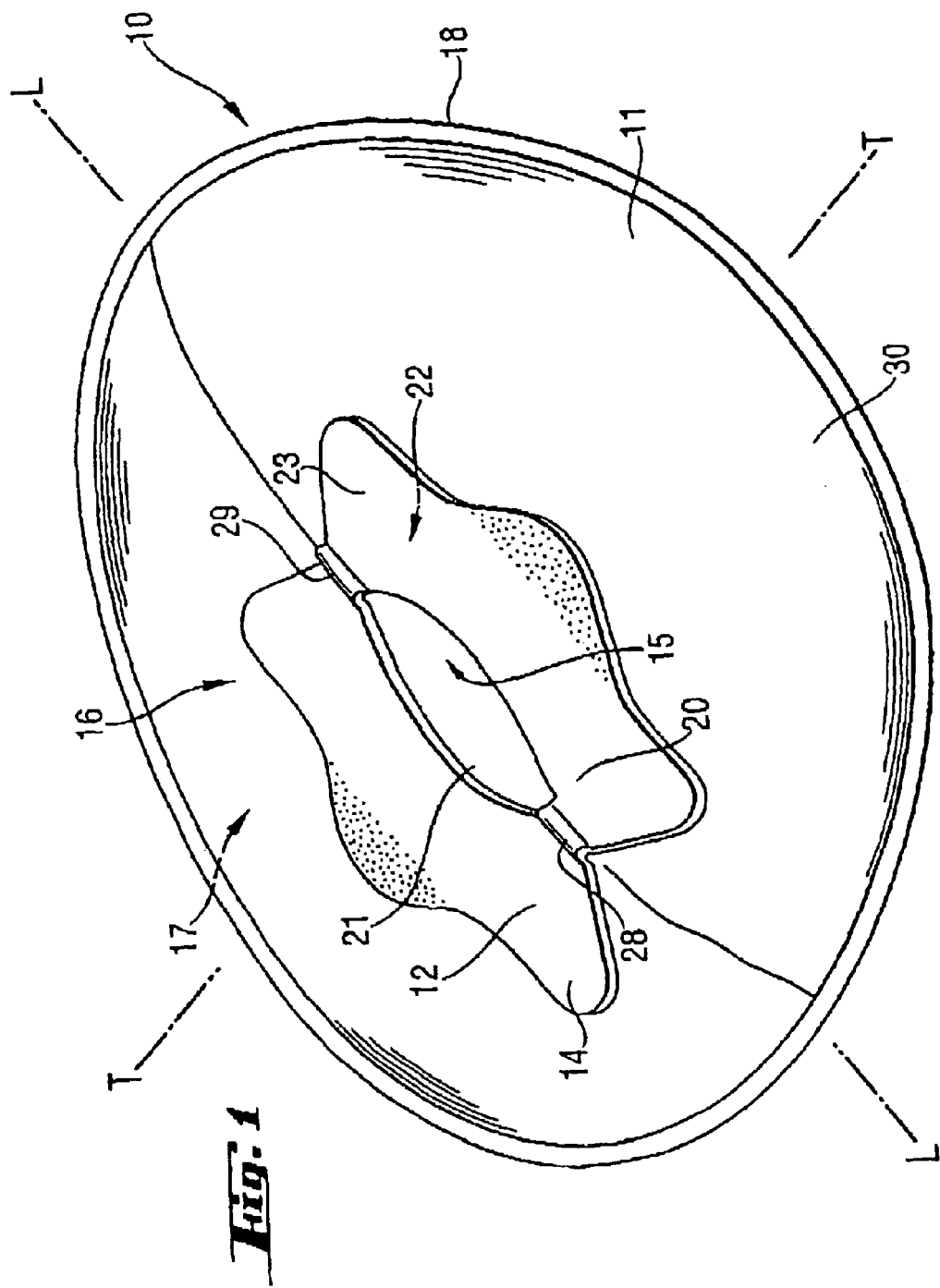
FIG. 1 is a perspective view of a preferred embodiment of a faecal collection bag.

According to the present invention a diapering system (200) is provided which comprises a human waste collection bag component integral with an absorbent component, preferably a diaper component (100).

The term "integral", as used herein with regard to the components of a diapering system (200), denotes components which are attached to another, preferably by a means of juncture, most preferably permanently attached to another, so that the system can be handled, attached to the human body and worn as one part and not as a multitude of separate parts.

The term collection bag, as used herein, encompasses the collection bag component of the diapering system and denotes the whole functional entity, i.e. not only the bag (11), but also the associated parts, such as the flange (12).

The collection bag is liquid resistant and preferably liquid impervious. A collection bag filled with faeces will essentially retain those faeces even if not being fully liquid impervious. In one aspect this is due to the non-liquid nature of typical faeces. In another aspect this is due to the positioning of the collection bag under the topsheet of the diapering system (200) in preferred embodiments of this invention. Hence, preferably the undesirable contact of faeces with the skin of a wearer is not only hindered by the material of the collection bag, but further hindered by the material of the diapering system (200) topsheet, so that the relevant level of liquid resistance is provided by the material of the collection bag in combination with material of the diapering system (200) topsheet. It has been found that a collection bag provided from a single layer of non-woven material works well for a faecal collection bag (10). For a urine collection bag it is preferred that the material of the collection bag at least in combination with the material of the diapering system (200) topsheet is liquid impervious.

The aperture (21) of the collection bag (11) is preferably only a small opening, in that the circumference of the aperture (21) as measured along the inner periphery of the flange (12) is preferably smaller than at least one circumference measured in any direction along the inner layer of the bag (11) material. Preferably the circumference of the aperture (21) measures no more than 90%, more preferably no more than 80%, yet more preferably no more than 70%, yet more preferably no more than 50%, most preferably no more than 30% of the smallest circumference measured in any direction along the inner layer of the bag (11) material. Such a small aperture (21) is beneficial in suppressing leakage and malodour.

Preferred embodiments of the present invention are described in the following paragraphs, while the human waste collection bag component (FIGS. 1 and 2) and the absorbent component (FIG. 3) are described thereafter.

In some preferred embodiments of the present invention the absorbent component and the human waste collection bag do not have any common components apart from those which provide the juncture. The juncture may comprise points of juncture or one or more lines or curves of juncture provided by means known in the art, such as thermo-bonding, ultrasonic bonding, adhesive means, stitching, thermo-crimping, cold crimping.

In other preferred embodiments of the present invention elements or portions of elements are comprised by both the human waste collection bag and the absorbent component. For example, preferably the backsheet of the diapering system (200) is continuous and hence comprised by both components. In another preferred embodiment the topsheet of the diapering system (200) is continuous and hence comprised by both components.

Figure 4:
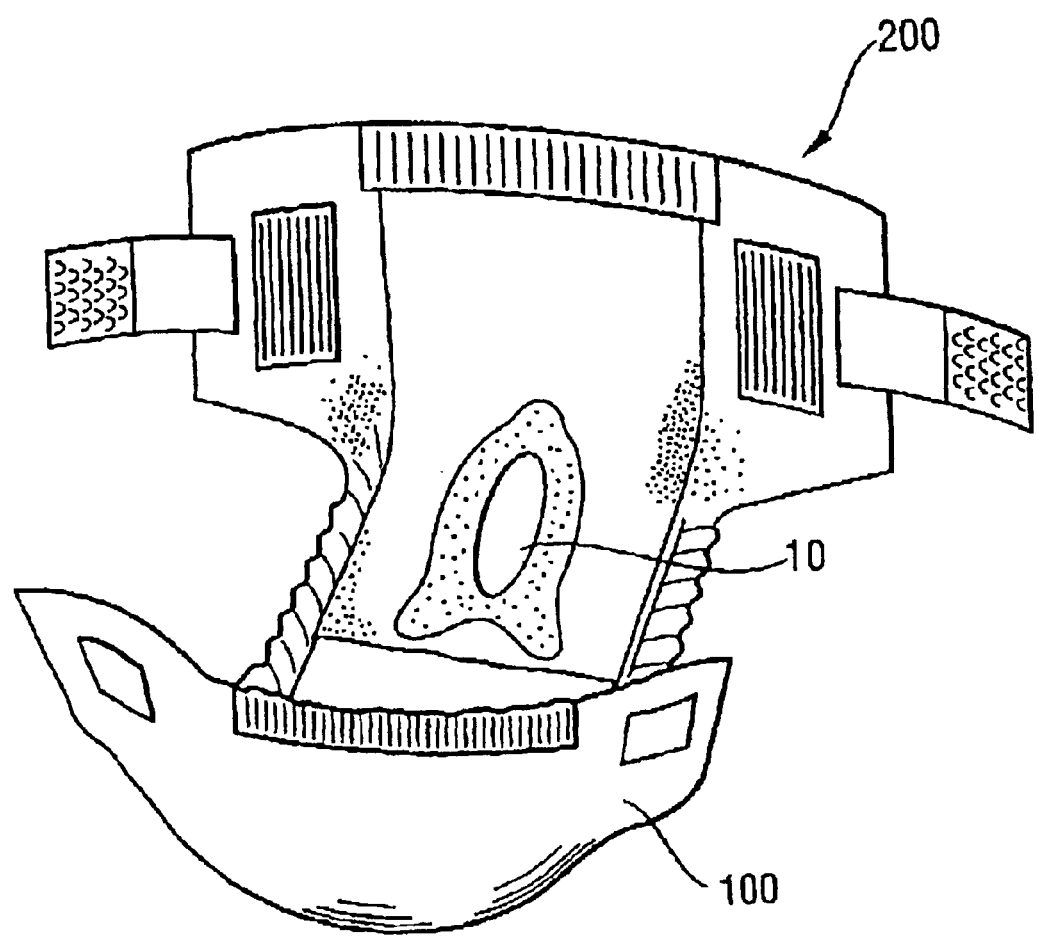
FIG. 4 is a perspective view of a diapering system provided with a faecal collection bag.

FIG. 4 shows a preferred embodiment of the present invention. In this embodiment a diapering system (200) is provided from a diaper component (100) as an absorbent component and a faecal collection bag (10). The diaper component (100) essentially comprises a topsheet, a backsheet and an absorbent core disposed in-between. The faecal collection bag (10) is disposed generally in the area of the diapering system (200) which is adjacent to the anus of the wearer when the diapering system (200) is worn. In this preferred embodiment no absorbent core material is present in this area of the diaper component (100). In this preferred embodiment the topsheet and the backsheet are comprised by the diaper component (100) as well as by the faecal collection bag component (10) of the diapering system (200). Hence, the topsheet is provided with an aperture which comprises the aperture of the faecal collection bag (10), i.e. the periphery of the aperture of the faecal collection bag (10) is within the periphery of the aperture of the diaper topsheet.

In preferred embodiments of the present invention the bag (11) of the faecal collection bag component (10) is positioned between the backsheet and the topsheet of the diaper component (100). Preferred embodiments of the present invention comprise those in which the bag (11) of the faecal collection bag (10) is positioned between the topsheet and the absorbent core and those in which the bag (11) of the faecal collection bag (10) is positioned between the absorbent core and the backsheet. In the latter embodiment the absorbent core (58) is provided with an orifice to allow the transfer of human waste from the aperture of the faecal collection bag (10) into the bag (11).

In highly preferred embodiments of the present invention there is no absorbent core provided in the area of the faecal collection bag (10) of the diaper component (100). Since faeces will to a large extend and preferably fully be contained in the faecal collection bag (10), absorbent core is only or predominately only needed to store urine. Therefore, sufficient absorbent core can be provided in the area generally adjacent to the uro-genital area of the wearer. For the same considerations in preferred embodiments of the present invention comprising a urine collection bag, no absorbent core is adjacent to the uro-genital area. In such embodiments the outer layer of the wearer facing portion (16) of the bag (11) and the outer layer of the garment facing portion (17) of the bag (11) are substantially not in direct contact with absorbent core. Absence of absorbent core in these areas allows the design of a less bulky product, which hence provides more wearing comfort.

The provision of the faecal collection bag (10) in any of the above described positions will make the faecal collection bag (10) integral with the diaper component (100), for example since portions of the faecal collection bag component (10) are positioned under the topsheet of the diaper component (100).

However, in preferred embodiments of the present invention the faecal collection bag component (10) and the diaper component will further be permanently attached to one another by means known in the art, such as thermo-bonding, ultrasonic bonding, adhesive means, stitching, thermocrimping, cold crimping. For example, portions of the bag (11) of the faecal collection bag component (10) may be attached to any portion of the diaper component (100), preferably to the topsheet, the backsheet or the absorbent core.

If the absorbent component is a diaper component, the diapering system (200) may comprise leg cuffs (62) as typically present in a conventional diaper and described in U.S. Pat. No. 3,860,003 and in WO 93/16669, whereas in another preferred embodiment the diapering system (200) does not comprise leg cuffs (62). Since the faecal collection bag (10) of this embodiment has been found to reliably collect all faeces and since the absorbent component provided outside the bag (11) has been found to reliably collect all urine and other bodily discharges, there is no need to design the diapering system (200) for a tight fit and sealing with the body as to prevent leakage of human waste. Therefore this preferred embodiment of the present invention allows a looser and more comfortable fit as compared with conventional diapers while exhibiting the same or even better performance in collecting human waste.

Moreover, the smaller form and absence of parts such as leg cuffs (62) allows to save material and storage costs. Furthermore, it is contemplated to provide a diapering system (200) according to the present invention without or with less waist elastics and without or reduced other elastics typically comprised by a conventional diaper. However, diapering systems (200) comprising leg cuffs and other elastic components are also preferred.

Figure 3:
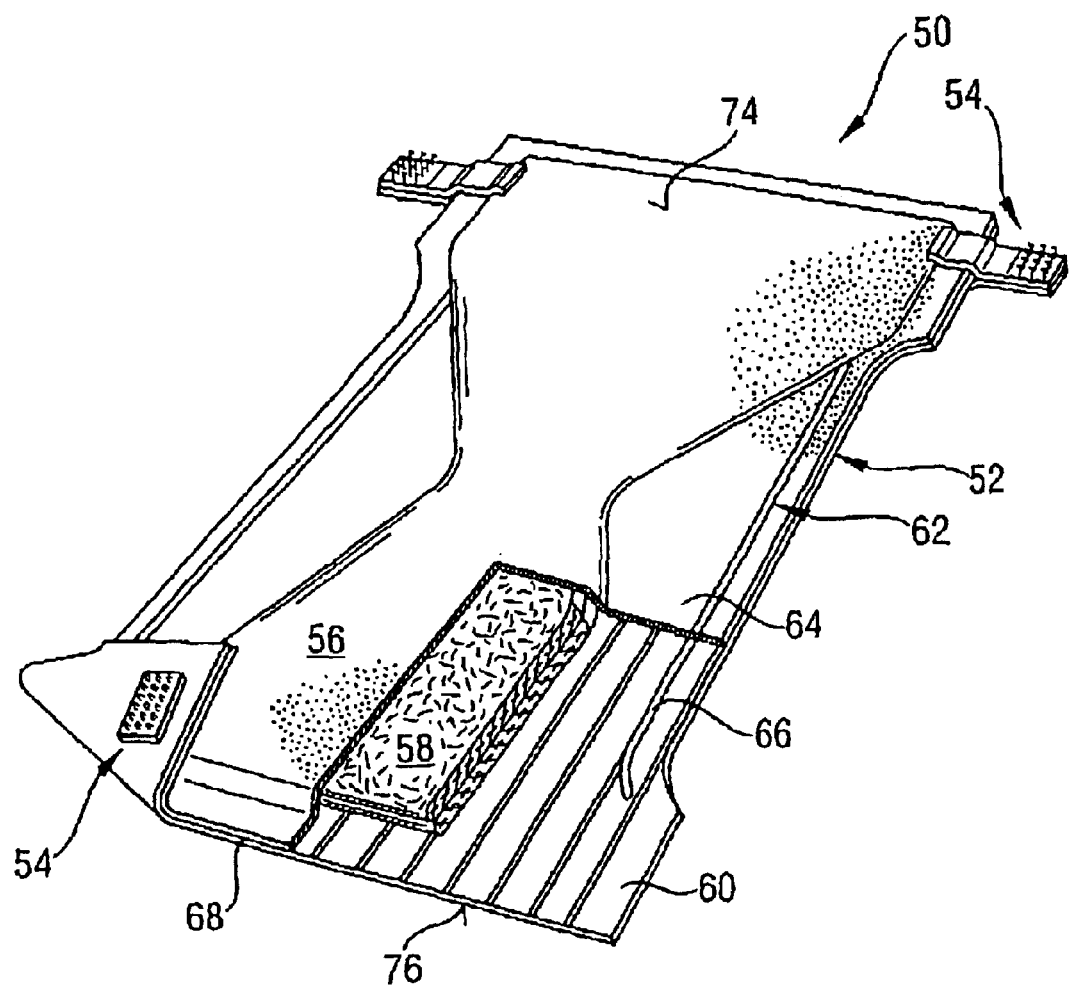
FIG. 3 is a partially cut-away perspective view of a diaper component to be used in accordance with the present invention.

The diapering system (200) of the present invention can be placed on the human body more easily than single human waste collection bags since it has the overall form of a body fitting garment. Therefore, it can be provided with means to secure it around the lower body of the wearer such as fastening devices, preferably fastening tabs (54) as shown in FIG. 3 and disclosed in U.S. Pat. No. 3,860,003 and in WO 93/16669. This allows the use of more skin friendly adhesive for the flanges, since such adhesives do not need to provide strength to hold the diapering system in place as a whole. Hence, preferred diapering systems (200) comprise means for attachment to the human body in addition to the means for attachment comprised by the flange (12) (typically an adhesive). For example, according to the present invention a diapering system (200) may be provided which comprises an attachment means not being comprised by the flange (12).

Since the diapering system (200) of FIG. 4 largely resembles in shape an undergarment, such as a panty, it can be worn without wearing any further undergarments. Some wearers experience this as more convenient and comfortable.

The Human Waste Collection Bag Component

Figure 2:
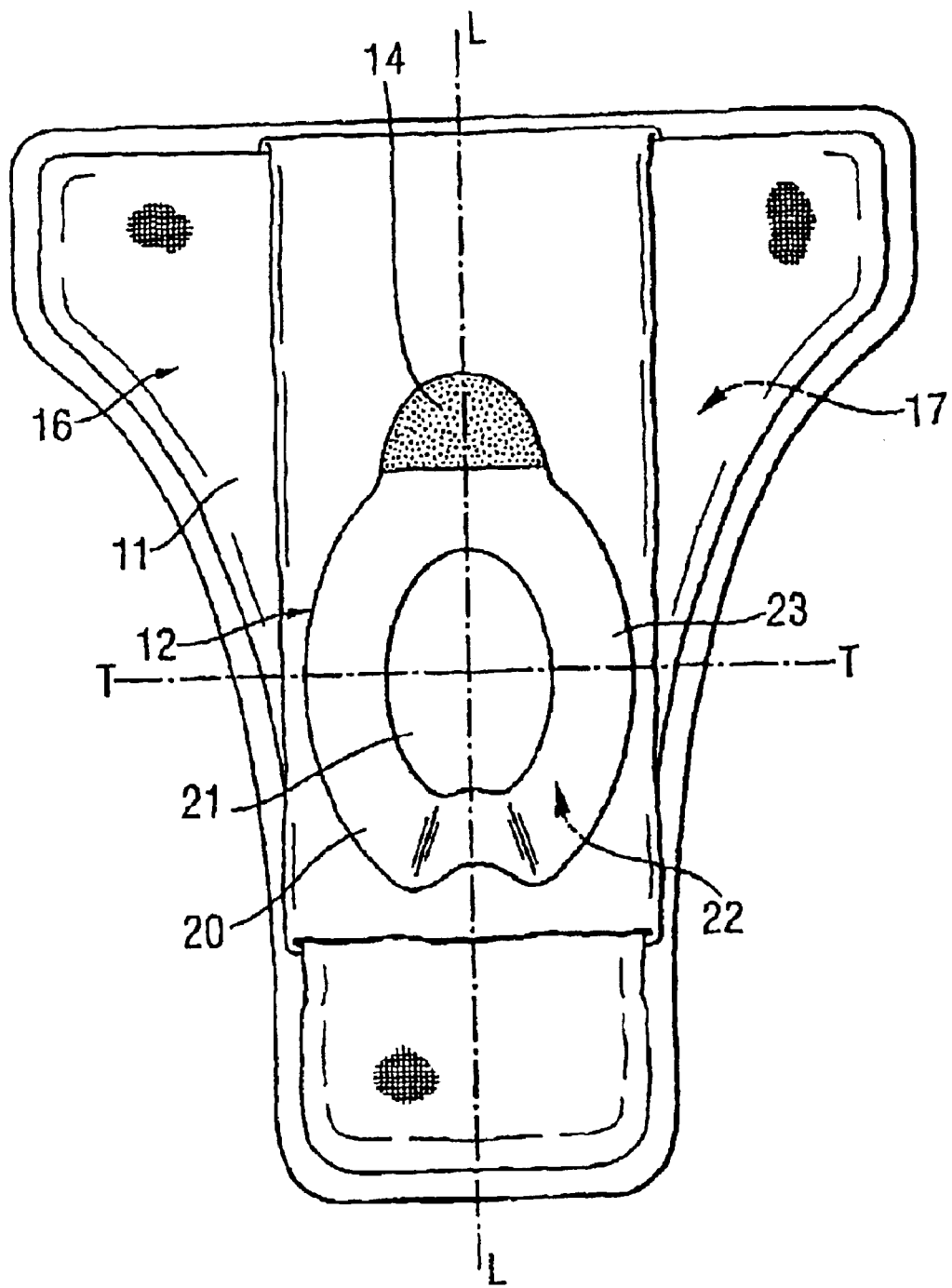
FIG. 2 is a top view of a preferred embodiment of a urine collection bag. L denotes the longitudinal direction and T denotes the transversal direction.

Human waste collection bags comprise faecal collection bags (10) and urine collection bags. As used herein any reference to human collection bags, faecal collection bags (10) or urine collection bags is to be understood as encompassing any such bags which are components of diapering systems (200), also referred to as human waste collection bag components, faecal collection bag components (10) or urine collection bag components, respectively. Both types of collection bags can comprise similar or alike components and materials and are therefore described together. A typical faecal collection bag (10) is shown in FIG. 1 and a typical urine collection bag is shown in FIG. 2. Faecal collection bags (10) are designed for attachment to the anal area and mainly used for collecting faeces, whereas urinary collection bags are attached to the urinary duct and mainly used for collecting urine. All of the above human waste collection bags are preferably designed for single use and disposal thereafter.

Typically human waste collection bags comprise a bag (11) having an aperture (21) and a flange (12) surrounding the aperture for preferably adhesive attachment to the perianal area of a wearer as visible from FIG. 1. Any human waste collection bag known in the art can be provided according to the present invention.

The bag (11) as used herein is a flexible receptacle for the containment of excreted faecal matter or urine. The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention the bag (11) material can comprise one or multiple layers, preferably two or three layers. The layer on the inside of the bag (11), which will typically at least partially come in contact with faecal material or urine is called the inner layer. The outermost layer of the bag (11), which will typically at least partially come in contact with the skin to the wearer and the garments of the wearer, is called the outer layer.

The layers of the bag (11) material may comprise any material, preferably so that the bag (11) is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag (11) material may comprise a non-woven layer. Such material layers present an uneven surface to the skin of the wearer and thus reduce significantly the problem of occlusion and greatly improve skin healthiness.

In one preferred embodiment of the present invention the bag (11) material comprises two layers. Preferably the outer layer comprises a non-woven layer and the inner layer comprises a film.

In yet another preferred embodiment of the present invention, the bag (11) material comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) material may be hydrophobic or hydrophilic. If the bag (11) material does not comprise a film layer, preferably at least one non-woven layer is hydrophobic. As a consequence, fluid penetration is resisted through the wearer facing portion (16) and the garment facing portion (17) of the human waste collection bag. As used herein the wearer facing portion (16) is to be understood as the portion of the bag (11) generally facing towards the wearer and the garment facing portion (17) is to be understood as the portion of the bag (11) generally facing the garment of the wearer. Both portions are typically in contact with other portions of the present diapering system (200) and not in direct contact with the wearer or any of the wearers garments, respectively. If the bag (11) material comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, cationic, non-ionic and amphoteric surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

According to the present invention, depending on the shape of the bag (11) required, the bag (11) may be provided from a unitary piece of material or a number of separate pieces of material, which may be identical or different and which are sealed at their respective peripheries. The preferred shape of the bag (11) depends in particular on the intended use thereof, i.e. whether the device is intended for bedridden patients or active patients suffering from incontinence or requiring an artificial bowel or for infants.

The bag (11) described herein preferably have a wearer facing portion (16) and a garment facing portion (17), which both comprise separate pieces of material. The wearer facing portion (16) and the garment facing portion (17) are sealed at the periphery of the bag (11), thus creating a bag peripheral rim (18). The wearer facing portion (16) and the garment facing portion (17) may each independently comprise more than one section of material. Preferably the garment facing portion (17) comprises only one section of material; most preferably also the wearer facing portion (16) comprises only one section of material.

The wearer facing portion (16), the garment facing portion (17) and the pieces of material comprised by either of these portions are secured to each other by means known to the man skilled in the art, such as adhesive, thermobonding or pressure bonding in order to provide the desired bag configuration. The rim (18), at which the wearer facing portion (16) and the garment facing portion (17) are sealed together, may be provided inside the bag (11) rather than outside the bag (11), thus being coextensive with the inner surface (15) of the bag (11) rather than with the outer surface (30) of the bag (11).

Hence a variety of shapes of the bag (11) is within the scope of the present invention. Particularly, preferred shapes are flat circular type bags, cone shaped bags, truncated cone shaped bags and pyramidal or truncated pyramidal shaped bags and flat T shaped bags. For faecal collection bags (10) the truncated cone shape is most preferred, whereas for urine collection bags the flat T-shape is most preferred.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag (11) or may be secured to the inner surface (15) of the bag (11). Any known techniques for securing absorbent material to nonwoven and film substrates may be used to secure the absorbent material to the inner surface (15) of the bag (11). The absorbent material may also be arranged to have any desired shape or configuration (e.g., rectangular, oval, circular, etc.).

The bag (11) is provided with an aperture (21) whereby faecal matter or urine is received from the body prior to storage within the bag (11) cavity. The aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction.

The flange (12) is attached to the bag (11) according to any means known to the man skilled in the art which may provide permanent or releasable attachment. Preferably however, the flange is attached to the bag (11) by adhesive. Typically, the bag (11) will be attached to the flange, towards the outer periphery of flange so as not to cause any obstruction for the entering faecal matter or urine.

The flange may be provided in any size depending on the wearer group for which the device is intended. Similarly the flange may be provided in any shape and preferably has a symmetrical shape preferably comprising a plurality of lobes (14).

The flange comprises a garment facing portion (22) and a wearer facing portion (23). In an preferred embodiment these are two large, substantially flat surfaces, however, the flange (12) may also comprise projections, a front projection (28) and/or a rear projection (29), in case of a faecal collection bag (10) designed to fit the perineal and/or coccygeal area of the wearer and in case of a urine collection bag designed to fit the genital and/or perineal area.

The flange (12) should be made of soft, flexible and malleable material to allow easy placement of the flange (12) to the perianal or uro-genital area. Typical materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimetres and a density of 5 to 250 g/m$^3$, more preferably 50 g/m$^3$. Other thermoplastic foam materials, or other suitable plastics sheet materials having the described properties of such foams (i.e., softness, pliability, stretchability, and contractability) might also be used. Preferably, the material of garment facing portion (22) of the flange (12) may extend into the defined aperture area so as to form a skirt or flap of material which prevents unintentional adhesion of the surface edges of the flange (12) defining the aperture (21) to one another during use.

According to the present invention the human waste collection bag further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconised paper. The adhesive (20) can cover the entire wearer facing portion (23) of the flange (12), more preferably the flange (12) has at least one, preferably two to six non-adhesive portions. These portions may be adhesive free or may contain inactivated or covered adhesives. As is evident from FIG. 1, the adhesive is in one preferred embodiment not applied to the entire wearer facing portion (23) of the flange (12), so as to provide lobes (14) on either side of the flange (12) which are non-adhesive and can thereby serve to facilitate placement and removal of the device whilst avoiding contact with the adhesive. These lobes (14) are however preferably also covered by the release means. Before application of the human waste collection bag to the skin of the wearer, the release means if present is removed.

According to the present invention any medically approved water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, whilst allowing for relatively painless application and removal, are formed from crosslinking polymers with a plastisicer to form a 3-dimensional matrix.

The adhesive (20) can be applied to the wearer facing portion (23) of the flange (12) by any means known in the art such as slot coating, spiral, or bead application or printing. Typically the adhesive (20) is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example, for human waste collection bags to be used for babies the amount of adhesive (20) may be less than for human waste collection bags designed for active adult incontinence sufferers.

The absorbent component

The absorbent component comprises an absorbent material. Preferred absorbent materials are listed below for a diaper component. Preferably the absorbent component comprises further a topsheet and a backsheet. Preferred topsheet and backsheet materials are also listed below for a diaper component. Preferably the absorbent material is disposed in-between the topsheet and the backsheet.

Preferred absorbent components comprise sanitary napkins, panty liners and adult incontinence pads, as disclosed for example in WO 91/16873 and WO 99/27877. A highly preferred absorbent component is a diaper component which comprises substantially all elements of a conventional diaper, which however comprises the adaptations described above (particularly a reduced amount of absorbent material, an orifice to transfer human waste into the human waste collection bag component and means of integration of the bag component). The preferred elements of a diaper component to be used for the diapering system (200) are described hereinafter with regard to a conventional diaper.

FIG. 3 is a partially cut-away perspective view of a conventional diaper (50). As is visible from FIG. 3, a preferred conventional diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the conventional diaper (50) opposite the outside surface (76) and in the embodiment shown is typically formed by the topsheet (56). In general, the inside surface (74) of the conventional diaper (50) is that surface coextensive with the outside surface (76) and which is for the greater part in contact with the wearer when the conventional diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the conventional diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibres. Preferably, it is made of a material that isolates the skin of the wearer from liquids retained in the absorbent core (58).

There are a number of manufacturing techniques which may be used to manufacture the topsheet (56). For example, the topsheet (56) may be a non-woven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

What is claimed is:

1. A diapering system comprising a faecal collection bag said faecal collection bag being integral with an absorbent component that is disposed outside of said faecal collection bag, wherein:

said absorbent component consists essentially of an absorbent core combining a superabsorbent polymer and a second material selected from the group consisting of meltblown polymers, airfelt, absorbent foams and combinations thereof, and both of said faecal collection bag and said absorbent component are disposed between a topsheet and a backsheet.

2. A diapering system according to claim 1, said faecal collection bag comprising a flange, wherein said faecal collection bag further comprises body compatible adhesive disposed on a wearer facing portion of said flange.

3. A diapering system according to claim 1 wherein said faecal collection bag further comprises absorbent material.

4. A diapering system according to claims 1, said faecal collection bag comprising a wearer facing portion and a garment facing portion, said wearer facing portion comprising an outer layer and said garment facing portion comprising an outer layer, wherein substantially no absorbent material is in direct contact with said outer layer of said wearer facing portion and said outer layer of said garment facing portion of said faecal collection bag.

* * * * *